United States Patent [19]
Phillips

[11] Patent Number: 5,464,441
[45] Date of Patent: * Nov. 7, 1995

[54] PROSTHETIC LEG

[76] Inventor: Van L. Phillips, P.O. Box 1873, Rancho Santa Fe, Calif. 92067

[*] Notice: The portion of the term of this patent subsequent to Jun. 8, 2010, has been disclaimed.

[21] Appl. No.: 74,040

[22] Filed: Jun. 8, 1993

Related U.S. Application Data

[63] Continuation of Ser. No. 464,201, Jan. 12, 1990, Pat. No. 5,217,500.

[51] Int. Cl.⁶ .................... A61F 2/60; A61F 2/62
[52] U.S. Cl. ................ 623/27; 623/52; 623/38
[58] Field of Search .................. 623/27, 28, 32, 623/38, 47, 50, 52

[56] References Cited

U.S. PATENT DOCUMENTS

| | | | |
|---|---|---|---|
| 42,799 | 5/1864 | Shepard | 623/54 |
| 61,780 | 2/1867 | Watson. | |
| 277,562 | 5/1867 | Furrer. | |
| 457,823 | 8/1891 | Rounds | 623/54 |
| 2,379,538 | 7/1945 | Meierhofer. | |
| 2,543,908 | 3/1951 | Guzey. | |
| 3,820,169 | 6/1974 | Long et al.. | |
| 4,268,922 | 5/1981 | Marsh et al.. | |
| 4,314,398 | 2/1982 | Pettersson. | |
| 4,461,103 | 7/1984 | Annovi | 36/121 |
| 4,547,913 | 10/1985 | Phillips. | |
| 4,822,363 | 4/1989 | Phillips. | |
| 4,883,493 | 11/1989 | Martel et al.. | |
| 4,911,724 | 3/1990 | Fikes. | |
| 4,959,073 | 9/1990 | Merlette. | |
| 4,994,086 | 2/1991 | Edwards. | |
| 5,037,444 | 8/1991 | Phillips. | |
| 5,116,381 | 5/1992 | Palfray. | |
| 5,156,631 | 10/1992 | Merlette. | |
| 5,181,932 | 1/1993 | Phillips. | |
| 5,181,933 | 1/1993 | Phillips. | |
| 5,201,775 | 4/1993 | Arbogast et al.. | |
| 5,217,500 | 6/1993 | Phillips | 623/38 |

FOREIGN PATENT DOCUMENTS

| | | | |
|---|---|---|---|
| 0012625 | of 1885 | United Kingdom | 623/27 |
| 1555581 | 11/1979 | United Kingdom | 623/27 |
| 2202448 | 9/1988 | United Kingdom. | |

*Primary Examiner*—David H. Willse
*Attorney, Agent, or Firm*—Knobbe, Martens, Olson, & Bear

[57] ABSTRACT

A prosthetic leg is characterized by an elongated, flat pylon operatively secured at its upper end to the wearer's leg and at its lower end to a prosthetic foot. The pylon is constituted by one or more leg elements which are fabricated from polymer impregnated and encapsulated laminates, including such laminates as carbon fibers and/or fiberglass or synthetic fibers such as Kevlar. The demountable connection of the leg elements permits interchangeability of leg elements to match the weight, stride and activity schedule of the wearer utilizing the prosthetic leg. Deformable adjustment is provided in juxtaposition to said leg elements whereby the flexibility of said pylon may be adjusted. To achieve or improve the desired flexure and energy-storage characteristics, the leg elements may be formed in a concavo-convex configuration.

13 Claims, 3 Drawing Sheets

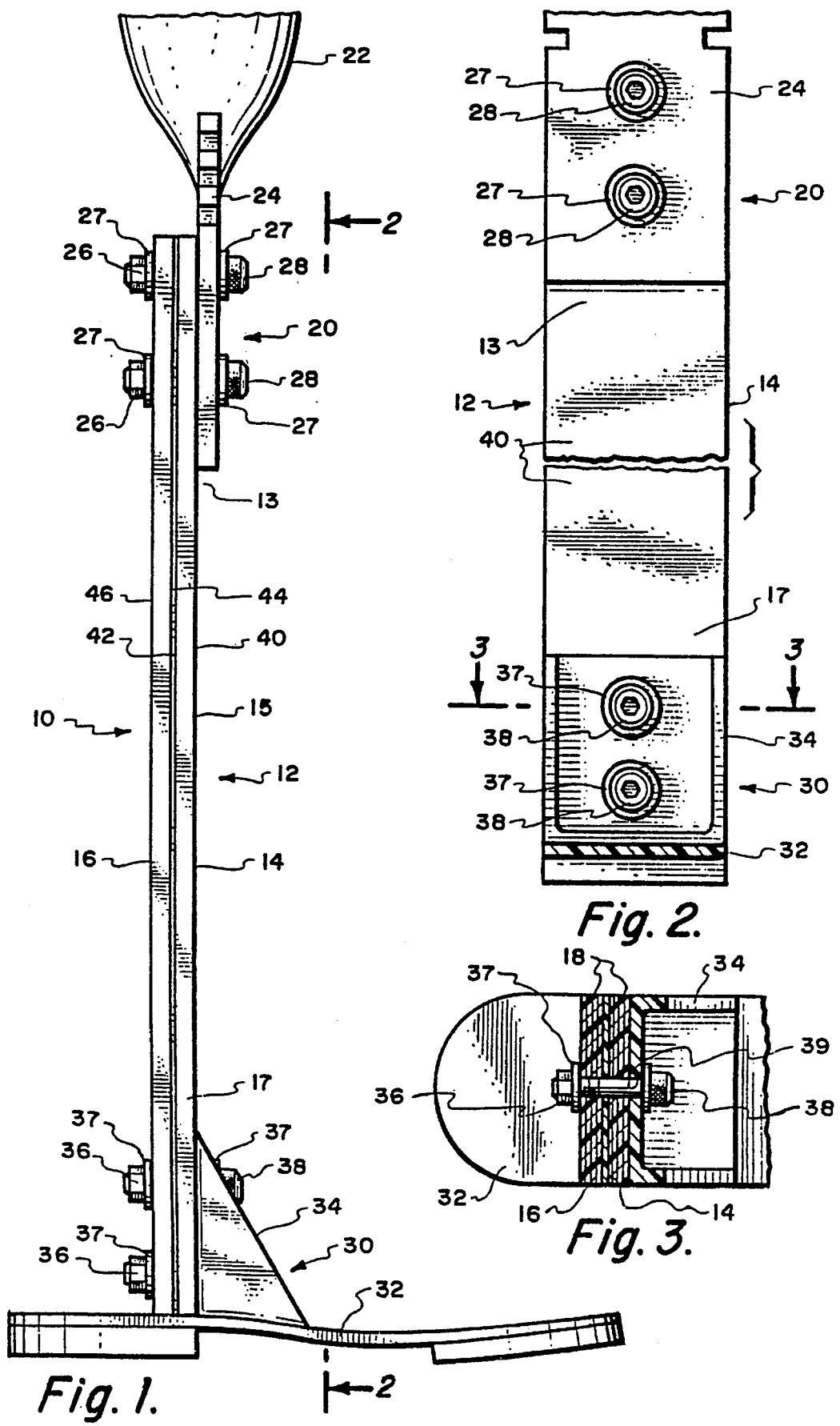

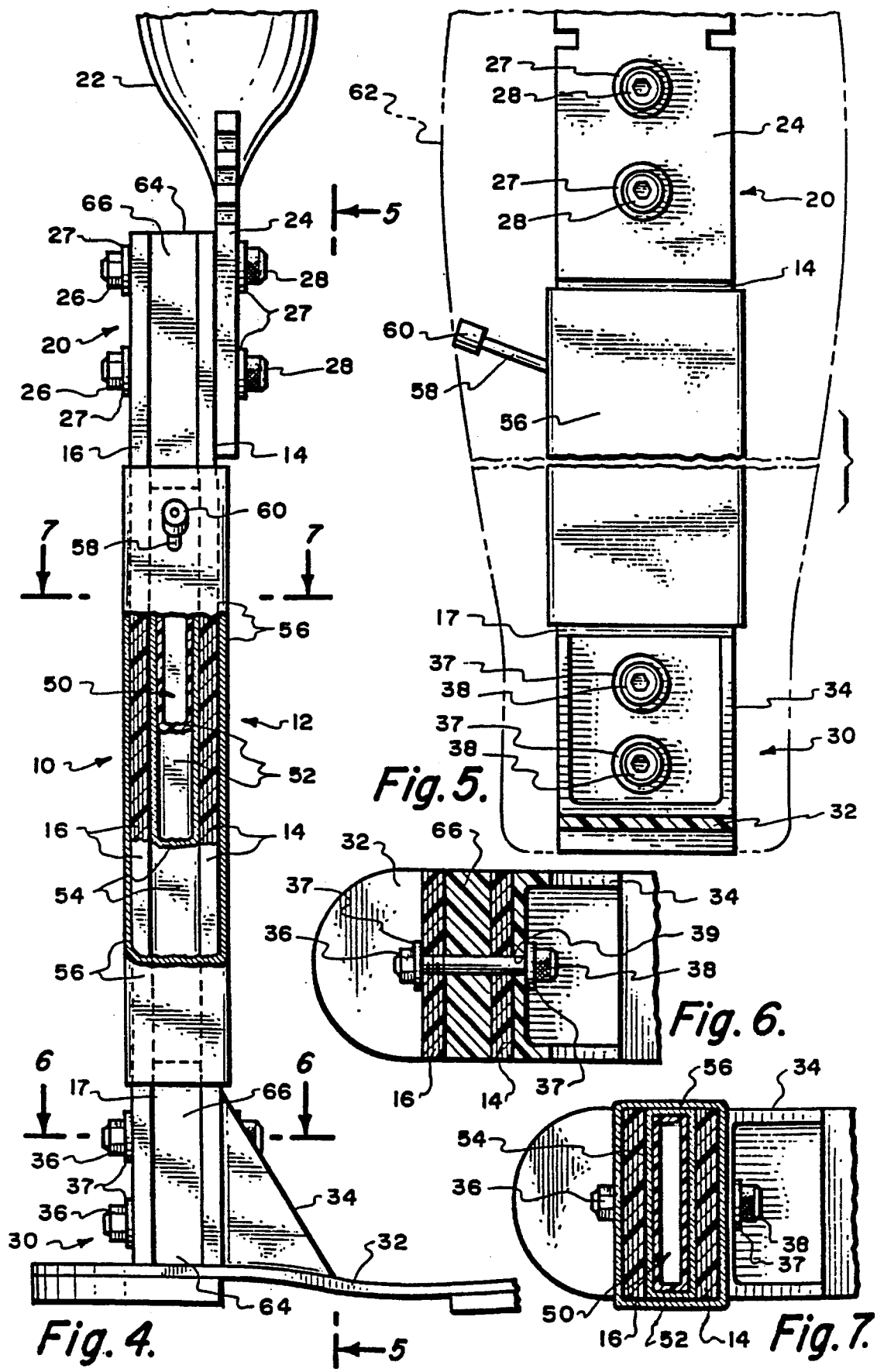

5,464,441

PROSTHETIC LEG

This application is a continuation of application Ser. No. 07/464,201, filed Jan. 12, 1990, now U.S. Pat. No. 5,217,500.

BACKGROUND OF THE INVENTION

This invention relates to leg prostheses in general, and specifically to a pylon to be used with a prosthetic foot. The pylon of the invention is characterized by a lightweight, elongated structure incorporating polymer impregnation of superimposed reinforcing laminae maintained in the desired configuration, such that any of a broad selection of prosthetic feet may be attached to the lower end of the pylon.

In addition, the desirable characteristics of strength and flexibility in the pylon member are enhanced by providing a multiplicity of the above-described elongated structures in juxtaposition to each other. This multiplicity of structures provides an interchangeable array from which the wearer may select an appropriate member for a particular activity. In alternative embodiments of the invention, deformable adjustment means, such as one or more inflatable bladders disposed between the aforesaid elongated structures, or other resilient means operatively engaged with the elongated structures, are provided to increase the ease and precision with which the flexibility of the prosthesis may be adjusted. The elongated structures may also be provided in a concavo-convex configuration, to improve or enhance the performance of the prosthesis.

Various types of foot and leg prosthetic devices are known in the prior art. Such devices generally include some form of attachment for coupling the device to the dorsal end of the limb and for extending to the ground to provide body support. Such prosthetic devices, particularly those intended to mount below the knee, are now frequently fabricated as an assembly having a leg region and footlike region, with some form of pivot therebetween so as to allow the foot portion to assume various angles with the leg portion and vice versa, as the wearer walks or goes through conventional motions. Devices of this general type are shown in U.S. Pat. Nos. 2,379,538, 3,400,408, 4,007,496, 4,089,072, and 4,161,042. In general the leg and footlike portions are usually rigid members.

My invention, in contrast, is compatible with a range of prosthetic feet and enhances the performance of such feet. Examples of such prosthetic foot devices include U.S. Pat. No. 2,075,583 to Lange, which incorporates a rubber form mounted in operative relationship with a rigid metallic core, and No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

These and other prosthetic foot devices have significant deficiencies, however, providing an opportunity for improved performance when the device of my invention is utilized; specifically, the component parts of the aforesaid foot prostheses, as in Lange, are too heavy and too rigid or, as in Poggi, are too massive and monolithic to respond properly to the nuances of stress-response gradients characteristic of the human foot.

These deficiencies are overcome to at least some degree in U.S. Pat. No. 4,547,913 for my invention relating to a "Composite Prosthetic Foot and Leg", and U.S. Pat. No. 4,822,363 for my invention relating to a "Modular Composite Prosthetic Foot and Leg". Those patents disclose certain concepts relating to a prosthetic foot characterized by a lightweight, unitary structure incorporating polymer impregnation of superimposed reinforcing laminae maintained in the desired configuration.

In addition, my aforementioned patents disclose interchangeable foot, heel and ankle portions which may be permanently or demountably associated with each other whereby the portions can be readily exchanged with correspondingly constructed portions. This exchangeability permits size adjustment or accommodation of different spring rates to suit the size of foot of the amputee or the stride and weight of the amputee, yielding an almost infinite range of combinations of spring rate and size to the amputee, and allowing a natural stride and resilience of gait which has not been obtainable by prior art prosthetic devices.

Some of the benefits of my inventions disclosed in my aforementioned patents inhere in the interchangeable, lightweight, laminar construction which provides selectable degrees of strength and flexibility in a given structure. My present invention enhances and accentuates those same benefits, and in addition, provides at least some degree of those benefits to wearers of conventional or non-laminate prosthetic feet.

OBJECTS AND ADVANTAGES OF THE INVENTION

It is, therefore, an object of my invention to provide a leg prosthesis which is characterized by an elongated leg element having an upper attachment section operatively secured to the wearer's limb and having a lower attachment section to which a prosthetic foot may be permanently or demountably associated. Both the leg and foot prostheses can be readily exchanged with correspondingly constructed leg and foot prostheses to provide size adjustment or different spring rates to suit the size of leg and foot of the amputee or the stride, height, weight, and activity level of the amputee. Therefore, a range of combinations of spring rate and size can be provided to the amputee, achieving a natural stride and resilience of gait, which has not been fully obtainable by prior art prosthetic devices.

Another object of the invention is the provision of a prosthetic leg of the aforementioned character in which the leg element of the prosthesis is fabricated from superimposed laminates maintained in operative relationship by an encapsulating polymer, and further in which said leg element is susceptible to bending stress determined by the number of the laminates and polymers in the respective element. Thus, the leg element is encapsulated in a polymer and capable of spring stress response as loads are imposed thereupon during the utilization of said leg.

A further object of the invention is the provision of a prosthetic leg element of the aforementioned character which consists of continuous, integrally and simultaneously formed upper, middle, and lower sections, said sections being fabricated as a unitary structure by polymer impregnation of superimposed reinforcing laminae maintained in the desired configuration of said leg element and said sections being capable of spring stress generated energy storage whereby the subjection of the prosthetic foot to bending moments will cause uniform transmission of spring stress through said sections of said leg element.

Another object of the invention is the provision of the aforesaid leg prosthesis, in which a multiplicity of said leg elements may be utilized in combination with each other to vary the resistance of said leg prosthesis to loads imposed upon the prosthetic foot associated therewith. The concept of the multiplicity of leg elements includes the provision of leg elements characterized by different spring rates, which permits the resistance of the total combination to deflection to be precisely adjusted to the weight, activity level and other characteristics of the individual for whom said leg is being adjusted.

It is a further object of my invention to provide a prosthetic leg element of the aforementioned character which provides additional control and adjustability of the flexibility of the prosthetic leg of my invention through the incorporation of deformable adjustment means such as one or more inflatable bladders juxtaposed with the aforesaid multiplicity of leg elements, whereby the flexibility of the prosthesis is varied by increasing or decreasing the pressure in the aforesaid bladder or bladders. In a preferred construction, these bladders are easily accessible and may be adjusted at virtually any time by the wearer. Alternatively, similar adjustability benefits are provided by other resilient means such as elongated spring constructions or natural or synthetic rubber members disposed between the leg elements.

The polymers utilized to encapsulate the fibrous laminae are characterized by elasticity and flexibility so that the leg prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic leg, after proper fitting of the leg to insure that it is properly balanced and of appropriate size, the prosthesis may be encapsulated in a suitably shaped cosmetic shroud. The shroud must be sufficiently flexible so as not to inhibit the free movement and flexure of the leg, but, because of the inherently resilient and stress-absorbing characteristics of said leg, little dependence is needed upon the ancillary cushioning action of the shroud.

Consequently, the leg of my invention is characterized by extreme light weight, instantaneous response to imposed loads and correspondingly instantaneous delivery of stored energy when the gait of the wearer indicates that such stored energy is to be released. Moreover, the leg may be readily mounted in operative relationship with conventional prosthetic feet and couplings, or with prosthetic feet of the type of my previously noted patents, and the response characteristics of the leg can be fine-tuned by the blending of multiple prostheses leg elements alone or in combination with deformable adjustment or resilient means to achieve the ultimate in operative response to the needs of the wearer.

Consequently, the wearer of the leg may engage in a wide variety of activities which were precluded in the past, or in activities in which the wearer's enjoyment was limited, because of the structural limitations and corresponding performance of prior art prostheses. Running, jumping and other activities are sustained by the leg and it may be utilized in substantially the same manner as the normal leg of the wearer. The wearer is able to adjust the flexibility of the leg at his or her discretion.

Other objects and advantages of the invention will be apparent from the following specification and the accompanying drawings, which are for the purpose of illustration only.

BRIEF DESCRIPTION OF THE DRAWINGS

FIG. 1 is a side elevation view of a prosthesis constructed in accordance with the teachings of the invention;

FIG. 2 is a fragmentary partially sectional front view, taken along line 2—2 of FIG. 1; and FIG. 3 is a partial plan view, taken along line 3—3 of FIG. 2.

FIG. 4 is a side elevation partially sectional view of an alternative embodiment of the prosthesis of the invention which includes an inflatable bladder;

FIG. 5 is a fragmentary partially sectional front view, taken along line 5—5 of FIG. 4;

FIG. 6 is a partial plan view, taken along line 6—6 of FIG. 4;

FIG. 7 is a partial plan view, taken along line 7—7 of FIG. 4; and

DESCRIPTION OF PREFERRED EMBODIMENTS

Figure 8:
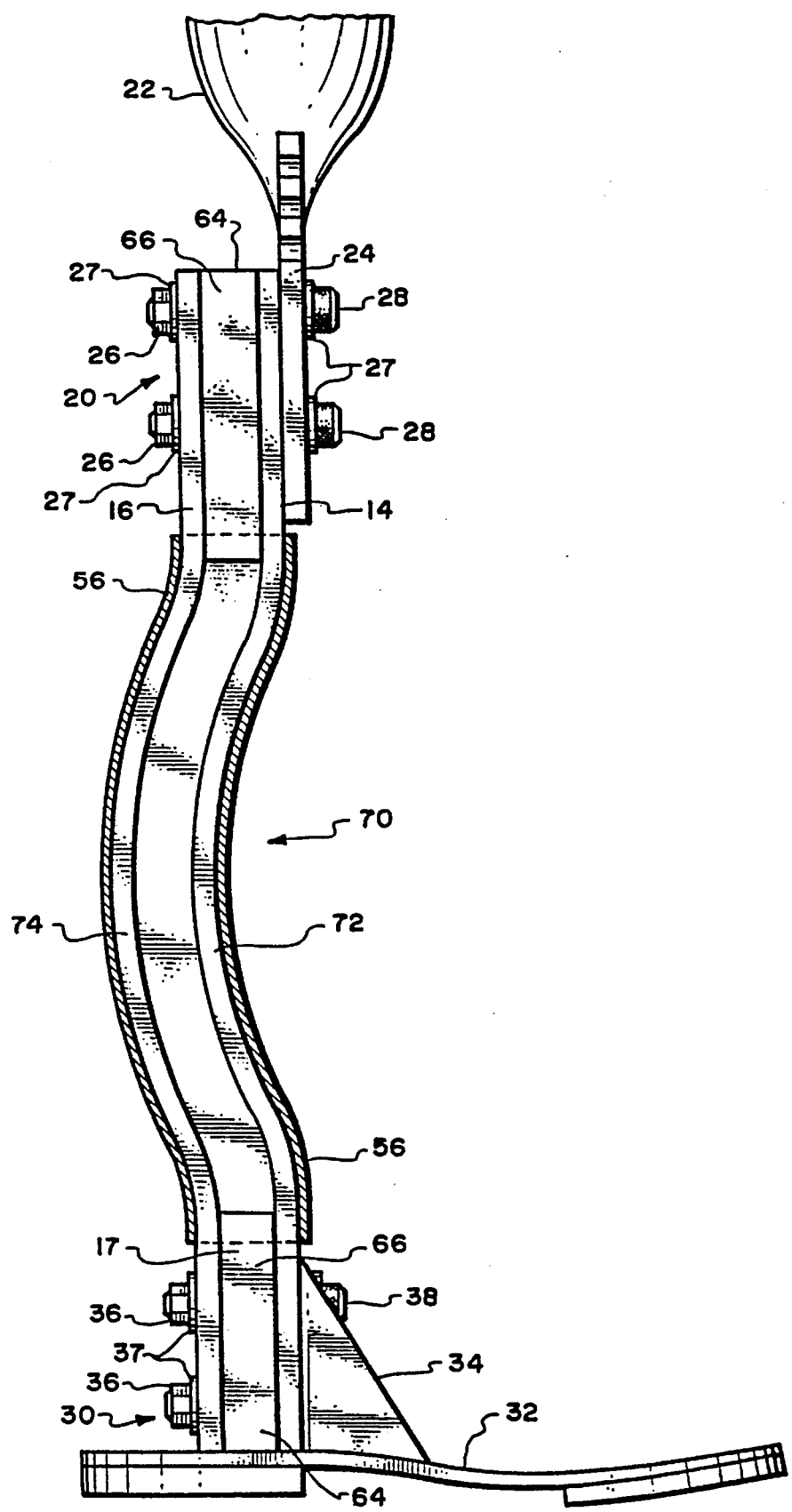
FIG. 8 is a side elevation partially sectional view of an alternative embodiment of the prosthesis of the invention which illustrates a concavo-convex configuration for the leg elements.

Referring to the drawings, and particularly to FIG. 1 thereof, I show a leg prosthesis 10 constructed in accordance with the teachings of the invention and including an elongated, flat pylon 12 constituted in the preferred embodiment by leg elements 14 and 16. Those skilled in the art will understand that the invention may be practiced with only one element 14 or 16, or with additional elements, as more thoroughly discussed herein. The elements 14 and 16 include upper sections 13, middle sections 15, and lower sections 17. The sections 13, 15, and 17 of the leg elements 14 and 16 are formed integrally with one another and simultaneously by the incorporation of a plurality of laminae 18, FIG. 3, embedded in a hardened, flexible polymer, similar to the fabrication methods taught in my above-noted prior art patents.

The leg prosthesis 10 further includes upper attachment means 20 constituted in the preferred embodiment by a socket 22 to receive the stump of the wearer of the prosthesis, a rigid connecting plate 24 attached to the socket 22, and nut 26, bolt 28, and washer 27 combinations to operatively and demountably connect the plate 24 and the leg portion 12. Suitable holes, similar to the holes 39 in FIG. 3, are provided in the rigid plate 24 and in the upper sections 13 of the leg elements 14 and 16 to permit the assembly of the various components. If indicated, the plate 24 and the leg elements 14 and 16 can be permanently secured to each other, as by epoxy adhesive or the like.

The leg prosthesis 10 of the present invention has lower attachment means 30 for securement of prosthetic foot means 32 thereto. Prosthetic foot means 32 may be selected from a range of prior art devices which may be suitably adapted for use with the leg prosthesis 10. Lower attachment means 30 includes, in the preferred embodiment, a relatively rigid bracket member 34 associated with foot means 32, and nut 36, bolt 38, and washer 37 combinations to operatively and demountably connect the bracket member 34 and the pylon 12. Suitable holes 39, FIG. 3, are provided in the bracket member 34 and in the lower section 17 of the leg elements 14 and 16 to permit the assembly of the various components. If indicated, the bracket 34 and the leg elements 14 and 16 can be permanently secured to each other, as by epoxy adhesive or the like.

The bracket 34 is positioned with respect to foot means 32 to provide optimum leverage and balance for the wearer during use of the prosthesis. The bracket 34 and the plate 24 are fabricated from a suitably strong, lightweight material such as graphite or a plurality of laminae embedded in a hardened, flexible polymer.

Those skilled in the art will understand that upper attachment means 20 and lower attachment means 30 have been described hereinabove merely by way of example, and that many alternative attachment means are available and may be utilized without departing from the scope of the invention. In particular, but not by way of limitation, a variety of structures may be utilized in place of the rigid plate 24 and the bracket 34.

The upper and lower attachment sections 13 and 17, when assembled respectively to the plate 24 and the bracket 34, are substantially rigid and capable of sustaining torsional, impact, and other loads impressed thereupon by foot means 32 and the wearer through the socket 22. In addition, the inherent rigidity of the attachment sections prevents them from being distorted in any way and causes the effective transmission of the aforesaid loads imposed thereupon between the socket 22 and foot means 32.

The leg elements 14 and 16 can be provided with different numbers of laminates to make them more or less compliant to loads transmitted between the socket 22 and foot means 32. Consequently, when confronted with various anomalies in an amputee, such as an overweight condition or excess activity levels, the basic structure of the leg elements 14 and 16, and more particularly the middle sections 15, can be materially modified to provide leg element action which is precisely adjusted to the needs of the amputee. Moreover, a variety of leg elements 14 and 16 can be made available to an amputee, allowing the flexibility of the prosthesis to be adjusted on the basis of the particular activity which the amputee is undertaking.

Moreover, when more than one leg element is utilized the compliance and other physical characteristics can differ materially from each other to provide nuances of movement and response not achievable by prior art devices.

The nut 26, bolt 28, and washer 27 combinations and the nut 36, bolt 38, and washer 37 combinations serve to secure the pylon member 12 in operative relationship with the rigid plate 24 and foot means 32, respectively. The aforesaid mode of affixation facilitates the assembly, combination, or dismounting of selected leg elements 14 and 16 in operative relationship with selected rigid plates 24, sockets 22, and/or foot means 32, thus permitting a wide range of different sizes and stress load response characteristics to be related to each other to accomplish the optimum function of the prosthesis 10 to accommodate to the maximum extent the needs of the wearer of the prosthesis.

The leg element 14, as best shown in FIG. 1 of the drawings, has a substantially planar forward surface 40 and a rearward surface parallel 42 thereto. Similarly, the leg element 16 has a substantially planar forward surface 44 and a rearward surface parallel 46 thereto. The leg elements are provided, as noted above, with holes in their upper and lower sections 13 and 17, so that the elements may be readily interchanged and combined to provide a selected spring rate and spring stress response in the prosthesis 10. The combination of parallel surfaces, nut and bolt combinations, and holes, permits the aforesaid interchangeability and combinability, in that the various elements 14 and 16 may be secured in operative relationship. While the elements 14 and 16 are shown in the preferred embodiment as having substantially planar forward and rearward surfaces 40, 42, 44, and 46, those skilled in the art will understand that any of a number of aligned cross-sectional configurations could be utilized in the pylon 12 and still be within the teachings of the invention. One such alternative configuration is shown in FIG. 8 and discussed more thoroughly hereinbelow.

For a given cross-sectional area of the pylon 12, the provision of operative alignment of the elements 14 and 16 achieves a greater flexibility for the pylon 12 than would a single element of equivalent cross-sectional area. That is, a wearer may utilize two elements which have a combined cross-sectional area equal to a single pylon, and the combination of the two elements provides equivalent strength to the wearer but provides greater flexibility than the single pylon. Similarly, utilizing three elements rather than one would provide even more flexibility.

As noted above, a multiplicity of elements such as elements 14 and 16 may be combined and/or available to a wearer to allow the wearer to select the appropriate spring rate and spring stress response of the prosthesis 10. This selection and combinability permits the ratio of strength to flexibility of the prosthesis to be controlled in a much more precise manner than is achievable with prior art devices. In addition, a multiplicity of pylons extends the fatigue life of the pylons by dividing the stress and loads which otherwise would be exerted on a single pylon.

In an alternative embodiment of my invention, FIGS. 4–7, the precision with which the flexibility of the prosthesis 10 is controlled is increased by incorporating deformable adjustment means 50 therein, for determining the flexural modulus of the leg elements of the prosthesis. The leg elements 14 and 16 are preferably spaced apart by lightweight spacer means 64 such as blocks 66 juxtaposed with upper and lower attachment means 20 and 30. The adjustment means 50 further preferably includes a bladder member 52 disposed in the resulting cavity between elements 14 and 16. The bladder member 52 is of sufficient size and has a minimum threshold pressure therein, so that the member 52 is in dynamic contact with the leg elements 14 and 16. Increasing the pressure in the bladder member decreases the flexibility of the prosthesis 10, and vice versa.

Those skilled in the art will further understand that the above-described spacing between the leg elements 14 and 16 can be achieved in a wide variety of constructions without departing from my invention, such as by the placement of the rigid plate 24 or an equivalent attachment means 20 between the elements 14 and 16.

In the preferred construction of this alternative embodiment, the bladder member 52 is manufactured as a rubber or urethane pouch inflated with air. The air pressure in the pouch can be adjusted through the provision of valve means 58, such as an air valve for regulating the pressure in a basketball or in a tire. In the preferred construction, valve means 58 includes an outer facing 60 positioned flush with the surface 62 of the above-described cosmetic shroud, FIG. 5. For cosmetic purposes, the outer facing 60 may be covered with a flesh-colored patch, not shown. If considerations indicate that the bladder pressure should not be adjustable by the wearer but only by a prosthetist or other professional, the access to valve means 58 can be restricted by locating it in abutment with one of leg elements 14 or 16. Alternatively, no valve means may be provided at all, necessitating the disassembly of the leg prosthesis in order to replace bladder means 50 when a different flexibility is desired.

Thus, the wearer may utilize any convenient air pump, such as a bicycle tire pump, to adjust the flexibility of the prosthesis 10 to a level suitable for the activity of the moment. This ease of adjustability has not been achieved by prior art devices, even those of my own prior invention.

Although the range of useful bladder pressures is certainly much wider, experiments indicate that air pressure in the range of 30 to 90 psi is sufficient to achieve the desirable characteristics of my invention.

Finally, the preferred construction of bladder member 52 further preferably includes an inner sleeve member 54 and an outer sleeve member 56, both manufactured as cloth woven tubes. As explained below, the sleeve members are of sufficient tensile strength to resist the hoop stresses placed thereupon by the positive pressure of the bladder member 52, but are flexible enough to permit the desired flexure of the leg prosthesis 10. A suitable material for the sleeve members has been found to be Spectra 1000, but any of a selection of tough, lightweight materials may be utilized. The sleeve members 54 and 56 extend substantially the length of the bladder member 52; that is, between or slightly overlapping the aforementioned spacer means 64.

The inner member 54 restricts the physical expansion of the bladder member 52, especially transversely of the leg elements 14 and 16, so that desirable bladder pressures can be achieved. The desired restriction of expansion in the direction of the spacer means 64 is accomplished by the presence of those spacer means. Those skilled in the art will understand, however, that the invention may be practiced without a sleeve member 54 and without the provision of spacer means 64 capable of the aforesaid restricting, if a sufficiently non-expandable bladder member 52 or other deformable adjustment means 50 is utilized.

The outer member 56 helps to retain the leg elements 14 and 16 in cooperating alignment with each other and with the bladder member 52. Numerous alternatives could be employed to achieve the desired cooperating alignment, including one or more retaining bands around the elements 14 and 16 along the length of bladder means 50. This cooperating alignment ensures that the effects of the bladder pressure are communicated to the leg elements 14 and 16 and impact the flexibility of the prosthesis 10. In alternative constructions, the outer sleeve member 56 or some other means of banding may be utilized to operatively engage one or more bladder members 52 to a single leg element 14, or to the exterior of a multiplicity of such leg elements.

Those skilled in the art will also understand that a multiplicity of deformable adjustment means 50 may be incorporated in the prosthesis of my invention without departing from the scope thereof.

In addition, those skilled in the art will understand that the above-described deformable adjustment means may include a wide variety of constructions, including by way of example and not by way of limitation, other resilient means such as various elongated spring constructions or natural or synthetic rubber members or some other deformable material such as foam rubber operatively disposed along the length of the leg element 14. Such alternative constructions and/or resilient means may be provided with a series of adjustable bands therearound to permit the aforementioned adjustment of the flexural modulus of the prosthetic leg.

The aforesaid resilient means or other deformable material may be bolted or otherwise operatively attached to the leg element or elements 14 and 16 intermediate upper and lower attachment means 20 and 30. For example, one or more elongated resilient members (not shown) may be provided to cooperate with the leg element or elements 14 and 16 during ambulation of the prosthesis, increasing the flexural resistance of the pylon 12. Such elongated resilient members are preferably not directly attached to the upper and lower attachment means 20 and 30, so that such additional members may be removed from or added to the prosthesis in a relatively easy fashion; that is, without the need to disassemble and reassemble the leg element 14 and the upper and lower attachment members 20 and 30.

A preferred method of engaging the additional elongated members with the leg element or elements 14 and 16 is the provision of one or more sets of aligned holes through the assembled leg element or elements and the additional elongated member or members. Such holes are each of sufficient size to accept a bolt which, with an associated nut and washer combination, accomplishes the desired engagement of the various structures comprising the pylon 12.

The aforesaid resilient means may also be disposed between the confronting surfaces 42 and 44 of the leg elements 14 and 16, whether such leg elements are relatively close together as in FIG. 1 or relatively spaced apart as in FIG. 4. Furthermore, one or more bladder members 52 may be included in any of such aforedescribed alternative constructions.

Thus, for a given selection of leg elements 14, the strength of the prosthesis 10 remains unchanged as the wearer adjusts the flexibility thereof by varying the bladder pressure, or otherwise adjusting the flexural modulus of the prosthetic leg with the deformable adjustment means or resilient means. In the construction shown in FIGS. 4–7, the wearer does not have to disassemble the prosthesis to accomplish the desired adjustment, but can instead simply adjust the bladder pressure as described above.

To further enhance or improve the flexibility, energy-storage and performance characteristics of the prosthesis 10, the leg portion 12 may be formed in a concavo-convex configuration. For example, in FIG. 8, a leg portion 70 includes leg elements 72 and 74 having concavo-convex sections centrally disposed along the length thereof. Such a curved cross-section reduces the energy necessary for initial flexure of the leg elements, as well as enabling such flexure to occur in a more smooth and controlled manner than is otherwise possible.

In addition, the aforementioned deformable adjustment means or resilient means may be operatively disposed between such leg elements, similarly to the structure illustrated in FIGS. 4–7.

In the preferred construction, FIG. 8, the leg elements are in a parallel relationship, although certain benefits of the invention may be appropriated by utilizing leg elements having non-parallel or mirror-image cross-sections. In such non-parallel constructions, it may not be desirable to enwrap the leg elements in a sleeve member 56, because such sleeve member could inhibit the desired deformation of the leg elements during ambulation. Such limited or unidirectional deformation may, however, be desirable in certain situations or for some persons.

Moreover, although the concavo-convex structure of FIG. 8 is shown to include two leg elements 72 and 74, those skilled in the art will understand that benefits of the invention may also be realized by incorporating such a concavo-convex cross-section into a single leg element or into a multiplicity of leg elements.

Additionally, and similarly to an alternative construction described above, resilient means such as one or more concavo-convex elongated members (not shown) of similar cross-sectional configuration to the cross section of leg element 72, may be operatively engaged with leg element 72 and/or leg element 74. Such similar cross-sectional configuration permits the additional elongated resilient members to be juxtaposed to, and to act in parallel with, the leg element 72. Such additional concavo-convex members are preferably not directly attached to the upper and lower attachment means 20 and 30, so that such additional members may be removed from or added to the prosthesis in a relatively easy fashion; that is, without the need to disassemble and reassemble the leg element 72 and the upper and lower attachment members 20 and 30.

A preferred method of engaging the additional elongated members with the leg element or elements 72 and 74 is the provision of one or more sets of aligned holes through the assembled leg element or elements and the concavo-convex elongated member or members. Such holes are each of sufficient size to accept a bolt which, with an associated nut and washer combination, accomplishes the desired engagement of the various concavo-convex structures.

It has been found that spacing the leg elements from each other as in FIGS. 4 and 8 creates an I-beam effect, which increases the strength and the stiffness of the leg prosthesis having leg elements of a given cross-sectional area. This increased strength thus permits the utilization of leg elements 14 and 16 that are thinner, narrower and lighter than would otherwise be possible. To achieve a desired strength while retaining the desired flexibility of the prosthesis, however, it may be desirable to incorporate the aforementioned concavo-convex configuration into the leg elements, as shown in FIG. 8.

The foregoing features of multiple leg elements, deformable adjustment or resilient means, and concavo-convex configuration may, of course, be combined in numerous ways to achieve a prosthetic leg with a particular set of performance traits or characteristics.

In the preferred embodiment, the elements 14 and 16 of the pylon 12 are all constructed without the necessity of tapering of the thickness thereof, although those skilled in the art will understand that the invention is not limited to such non-tapering construction.

The materials from which the elements 14 and 16 are fabricated must be such as to provide an energy-storing, resilient, spring-like effect. This is necessary because each engagement of foot means 32 with an adjacent surface impresses compression, torsional, and other loads upon the prosthesis 10 which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The leg elements 14 and 16 of the prosthesis are preferably molded as a unitary component and are carefully formed to provide for appropriate absorption of stress imposed thereupon. The configuration of elements 14 and 16 is of utmost importance and the laminates and the polymer or polymers from which the elements are fabricated must be resilient and capable of absorbing the compressive, torsional, and other stresses referred to hereinabove and of restoring the stored energy created by such stresses, in a natural manner, to the impacted surface which originally imposed such stresses upon the prosthesis 10.

It has been found that there is a limited number of polymers capable of sustaining the significant stresses and repetitive loads imposed upon the prosthesis 10, particularly in the light of the countless numbers of cycles to which the prosthesis 10 is subjected during normal, everyday use.

At present, the best materials for the prosthesis are a composite of high-strength graphite fiber in a high-toughness epoxy thermosetting resin system. There are several reasons for this: (1) high strength; (2) stiffness to weight ratio of graphite as compared to other materials; (3) the almost complete return of input or stored energy; (4) light weight; (5) high fatigue strength; and (6) minimal creep. As an alternative material, fiberglass/epoxy is a fair choice, but it is not as good as graphite because of lower fatigue strength and higher density. Kevlar is even less acceptable due to poor compression and shear strength, although it is the lowest density of those mentioned.

An important aspect of the polymers and laminates referred to hereinabove is that they are characterized by needed, but not excessive, flexural deflection under load, which characteristic permits the shock-absorption stress loading of the prosthesis 10 while maintaining sufficient stability to prevent the collapse of the pylon 12 while loads are imposed thereupon.

To achieve the relatively thin construction of the leg elements 14 and 16, the aforesaid polymers are utilized in conjunction with various laminating materials. Various types and various dimensions of fibrous laminae can be utilized to achieve the continuum required by the design of the elements 14 and 16 to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the mold to permit them to be encapsulated in the selected polymer.

Obviously, the number and thickness of the superimposed laminae and the lengths thereof, together with the thickness of the encapsulating polymer, determines the stress characteristics of the resultant elements 14 and 16 and, correspondingly, impacts the total weight of the prosthesis 10. As will be apparent from the discussion hereinbelow, the individual leg elements 14 and 16 are designed to specifically accommodate individuals having different foot sizes, different weights and different strides and the individual design of the elements 14 and 16 provides for matching, to an extent previously unknown in the art, the natural characteristics of the wearer's uninjured limb.

As previously mentioned, the upper section 13, the middle section 15, and the lower section 17 of each leg element 14 and 16 are formed integrally. The configuration of these sections is the means whereby bending and compressive loads imposed during impingement of foot means 32 upon an adjacent surface are absorbed and subsequently reimposed upon said surface. These upper, middle, and lower sections 13, 15 and 17 are so designed that they function, substantially, to permit some flexure of the leg elements 14 and 16 such that foot means 32 may pivot alternately forwardly and rearwardly with respect to the longitudinal axis of the elements 14 and 16. This flexure and pivoting can occur in a manner analogous to the manner in which the normal foot pivots about the normal ankle joint about an axis transversely of said ankle joint, and permits the wearer to experience a more natural gait and feel with the prosthesis than was possible with prior art prostheses.

Foot means 32 can be provided in different sizes to correspond to the size of the foot of the wearer of the prosthesis 10. When such different lengths are provided, corresponding reduction or increase in the number of laminae and thickness of taper, not shown, of the respective sections 13, 15, and 17 of the leg elements 14 and 16 can be made to provide for the proper flexure of said sections.

It will, of course, be obvious to those skilled in the art that, with respect to any embodiment of the invention, the fibrous reinforcements in the form of laminae plies encapsulated in the prosthesis may be fayed or tapered to accomplish a gradual transition in the flexural characteristics of the prosthesis as the number of plies is reduced in any area of the leg element.

Moreover, if a individual partakes in sports or other activities which subject the prosthesis 10 to greater loads than those of normal daily wear, a pylon 12 will be fitted which will accommodate for those greater loads.

The pylon 12 is substantially non-responsive to purely vertical compression loads. When subjected to bending moments, however, such as when a load is imposed at the toe of foot means 32, or when foot means 32 is subjected to forward or rearward forces during walking or running, the middle section 15 of the elements 14 and 16 deflects under such load.

Additionally, because the various sections 13, 15, and 17 of the pylon 12 are integrally fabricated, the aforesaid stresses are distributed throughout the length of the pylon 12. Consequently, there is no stress concentration, either in the impact phase when the adjacent surface is initially contacted by the wearer of the prosthesis 10, or when return of the accumulated forces stored in the prosthesis 10 is accomplished.

The aforementioned flexure of the leg elements 14 and 16 provides the capacity for increased surface area contact between foot means 32 and the adjacent surface during both the impact and delivery phases of the prosthesis 10. It will be noted that the elongated structure of the leg elements 14 and 16, together with their aforesaid flexure capabilities, provides for a relatively extended lever arm which achieves stress storage and stress reaction.

The preferred method of manufacturing the leg elements 14 and 16 of the prosthesis 10 is by a thermosetting molding process including the utilization of molds having properly shaped and sized cavities. The cavities are designed to receive the requisite number of laminates and the proper volume of polymer, such that the leg elements 14 and 16 are respectively unitary structures, with the upper, middle, and lower sections 13, 15, and 17 formed simultaneously within each respective leg element.

Unlike prior art unitary devices, the fitting of the prosthesis 10 involves the judicious adjustment of the prosthesis by the proper combination of elements 14 and/or 16 and/or deformable adjustment means 50 and foot means 32. Only when the proper correlation between the elements 14 and 16 and deformable adjustment means 50 and foot means 32 has been accomplished, can the cosmetic shroud, not shown, be installed upon the assembled, respective portions of the prosthesis 10.

By the prosthesis of my invention I provide a leg prosthesis which can be carefully matched to the weight, stride and physical characteristics of the wearer. This is accomplished by carefully balancing the respective physical characteristics of the leg elements 14 and 16 and the various sections thereof. In addition, further adjustment of the flexibility of the leg may be achieved by the incorporation of deformable adjustment means in the prosthesis.

Moreover, the assembled prosthesis is far lighter in weight than prior art prostheses since the inherent design and structure of the prosthesis, the materials used and the careful calculation of stress factors of the components of the prosthesis permit fine-tuning of the prosthesis to the needs of the wearer thereof. The leg of my invention may also be used in combination with numerous prior art prosthetic devices to improve the performance of such prior art devices.

The prosthesis of my invention has been described with some particularity but the specific designs and constructions disclosed are not to be taken as delimiting of the invention in that various obvious modifications will at once make themselves apparent to those of ordinary skill in the art, all of which will not depart from the essence of the invention and all such changes and modifications are intended to be encompassed within the appended claims.

I claim:

1. A leg prosthesis for supporting an amputee, said leg prosthesis having a proximal end and a distal end, said proximal end being secured to a socket for locating on the stump of an amputee, and said distal end being secured to a foot member, said leg prosthesis comprising:

a substantially vertically oriented and elongated pylon member providing substantially the sole support for loads incurred by said foot member, said pylon member being constituted by at least two substantially parallel planar leg elements operatively disposed between said socket and said foot member, said leg elements being independently capable of storing and releasing energy, and cooperating to provide a substantial portion of the energy storage and release characteristics of said leg prosthesis, said leg elements being flat with respect to one another and spaced apart substantially equidistantly along their lengths such that said leg elements bend at the same time and in substantial unison when loads are imposed on said prosthesis, said leg elements being secured together at said proximal end and at said distal end, and otherwise being separately formed and detachable such that various sized leg elements can be interchanged to provide the amputee with optimal adjustability.

2. The leg prosthesis of claim 1, wherein said leg elements are secured together by at least one nut and bolt member at said proximal end, and at least one nut and bolt member at said distal end, said nut and bolt members being removable to permit various sized leg elements to be utilized.

3. The leg prosthesis of claim 1, wherein each of said leg elements has a substantially rectangular cross-sectional shape, said leg elements being substantially thinner in the fore and aft direction and substantially wider in a direction perpendicular to said fore and aft direction.

4. The leg prosthesis of claim 1, wherein at least two spacer elements are provided between said leg elements, one of said spacer elements being located at said proximal end and another of said spacer elements being located at said distal end, said spacer elements separating said leg elements such that a void exists between said leg elements.

5. A foot and leg prosthesis for supporting an amputee relative to the ground, comprising:

a substantially vertically oriented pylon member having at least two parallel leg elements of substantially identical shape, said pylon member being capable of bending in the fore and aft direction and of storing and releasing energy;

wherein each of said leg elements comprises:

an upper attachment section which is substantially vertically oriented, said attachment section having a forward side and a back side, said forward side and said back side being substantially planar;

an intermediate section;

a lower attachment section being substantially vertically oriented, said lower attachment section having a forward side and a back side, said forward side and said back side being substantially planar; and wherein each of said leg elements are substantially flat with respect to one another such that a forward side of one of said leg elements faces a back side of another of said leg elements and such that said leg elements bend at the same time and in substantial unison when loads are imposed on said prosthesis;

a foot member secured to said pylon member, said foot member being secured to said lower attachment sections of said leg elements.

6. The prosthesis of claim 5, wherein at least two spacers are provided between said leg elements, one of said spacers being between said upper attachment sections of said leg elements and another of said spacers being positioned between said lower attachment sections of said leg elements.

7. The prosthesis of claim 6, wherein a void exists between said intermediate sections of said leg elements, said void permitting said leg elements to flex independently of one another.

8. The prosthesis of claim 5, wherein an outer sleeve member is positioned around the perimeter of said intermediate sections of said leg elements.

9. The prosthesis of claim 5, wherein said upper attachment sections of said leg elements are secured together by at least one nut and bolt member, and said lower attachment sections of said leg elements are secured together by at least one nut and bolt member.

10. The prosthesis of claim 5, wherein said foot member is secured to said lower attachment sections of said leg elements by at least one nut and bolt member.

11. The prostheses of claim 5 wherein said upper attachment section is secured to a socket for locating adjacent the stump of said amputee.

12. The prosthesis of claim 5, wherein said foot member is flexible and stores and releases energy during utilization of said prosthesis.

13. The prosthesis of claim 5, wherein said leg elements are detachable such that various sizes of leg elements can be interchanged to permit optimal adjustability of said prosthesis by said amputee.

* * * * *